United States Patent [19]

Edgar, Jr.

[11] Patent Number: 4,854,699
[45] Date of Patent: Aug. 8, 1989

[54] BACKSCATTER OXIMETER

[75] Inventor: Reuben W. Edgar, Jr., San Antonio, Tex.

[73] Assignee: Nippon Colin Co., Ltd., Komaki, Japan

[21] Appl. No.: 115,204

[22] Filed: Nov. 2, 1987

[51] Int. Cl.⁴ .......................... G01N 33/49; A61B 5/00
[52] U.S. Cl. ........................................ 356/41; 128/633
[58] Field of Search ...................... 356/39, 41; 128/633

[56] References Cited

U.S. PATENT DOCUMENTS

| | | | |
|---|---|---|---|
| 4,305,398 | 12/1981 | Sawa | 356/41 X |
| 4,446,871 | 5/1984 | Imura | 356/41 X |
| 4,463,762 | 8/1984 | Rubens | 356/41 X |
| 4,603,700 | 8/1986 | Nichols et al. | 356/41 X |
| 4,714,080 | 12/1987 | Edgar, Jr. et al. | 128/633 |

OTHER PUBLICATIONS

Takatani et al., "a Noninvasive Tissue Reflectance Oximeter, An Instrument for Measurement of Tissue Hemoglobin Oxygen Saturation In Vivo" Annals of Biomedical Engineering, vol. 8 #1, pp. 1–15, 1980.

Primary Examiner—Vincent P. McGraw
Attorney, Agent, or Firm—Matthews & Branscomb

[57] ABSTRACT

A noninvasive optical oximeter for measuring oxygen saturation of arterial blood. A sample of blood is illuminated with light at four different wavelengths. Light reflected by the blood is sensed by a photodetector and a plurality of output signals are created in response thereto. The reflected light at each of the four wavelengths is detected after contact with the blood and is correlated with the oxygen saturation of the patient's blood using mathematical relationships for arterial and venous oxygen saturation. The present invention provides a noninvasive backscatter oximeter which is capable of providing accurate indications of a patient's blood oxygen saturation without the need for obtaining prior information relating to the oxygen content of the patient's blood.

8 Claims, 1 Drawing Sheet

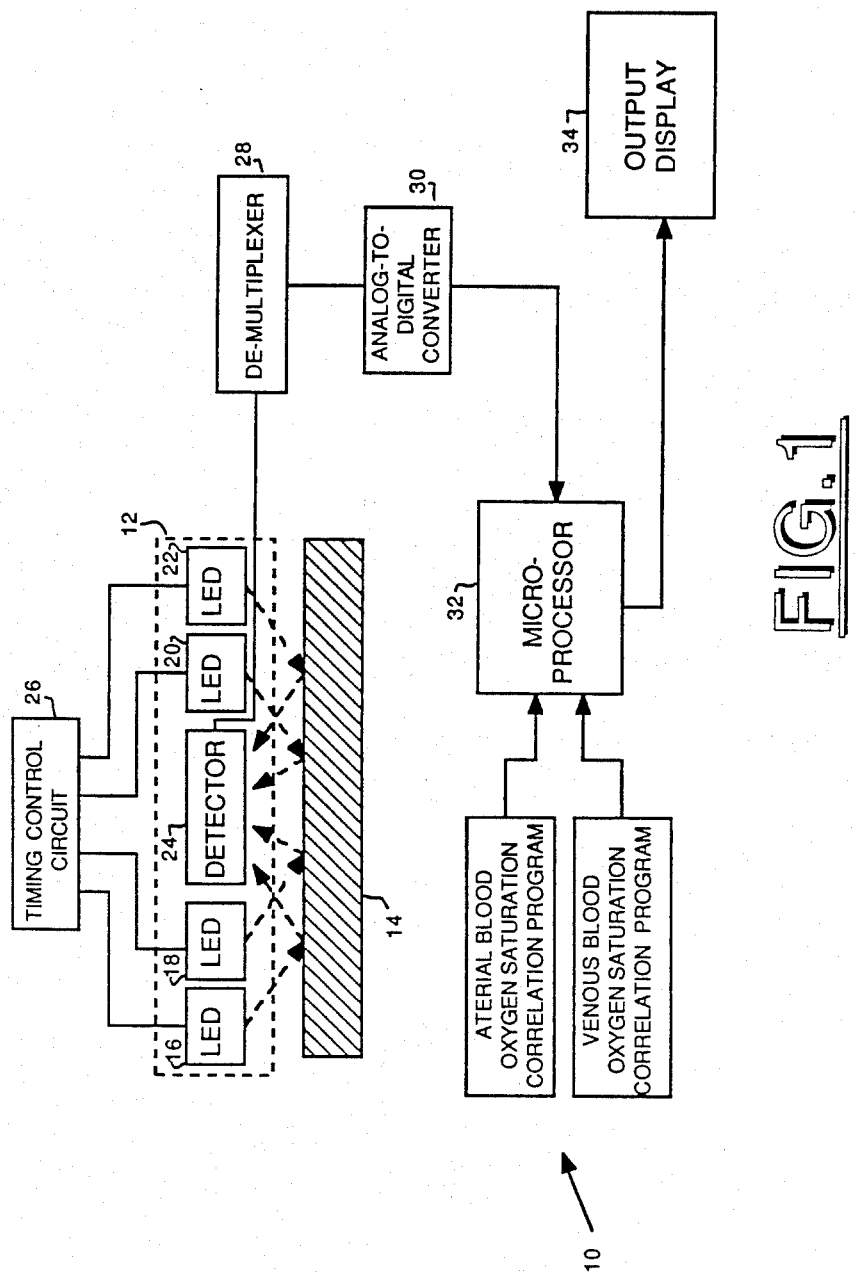

BACKSCATTER OXIMETER

FIELD OF THE INVENTION

The present invention relates generally to an oximeter which can be used to estimate the degree of oxygen saturation of a patient's blood. More specifically, the present invention provides a backscatter oximeter which is capable of providing accurate indications of arterial and venous oxygen saturations without the need for prior information relating to the oxygen content of the particular patient's blood.

BACKGROUND

It is well known that hemoglobin and oxyhemoglobin have different optical absorption spectra and that this difference in absorption spectra can be used as a basis for an optical oximeter. Most of the currently available oximeters using optical methods to determine blood oxygen saturation are based on transmission oximetry. These devices operate by transmitting light through an appendage such as a finger or an earlobe. By comparing the characteristics of the light transmitted into one side of the appendage with that detected on the opposite side, it is possible to compute oxygen concentrations. The main disadvantage of transmission oximetry is that it can only be used on portions of the body which are thin enough to allow passage of light.

Various methods and apparati for utilizing the optical properties of blood to measure blood oxygen saturation have been shown in the patent literature. Representative devices for utilizing the transmission method of oximetry have been disclosed in U.S. Pat. Nos. 4,586,513; 4,446,871; 4,407,290; 4,226,554; 4,167,331; and 3,998,550. Numerous other works have disclosed theoretical approaches for analyzing the behavior of light in blood and other materials. The following is a brief list of some of the most relevant of these references: "New Contributions to the Optics of Intensely Light-Scattering Materials, Part 1," by Paul Kubelka, *Journal of the Optical Society of America*, Volume 38, No. 5, May 1948; "Optical Transmission and Reflection by Blood," by R. J. Zdrojkowski and N. R. Pisharoty, *IEEE Transactions on Biomedical Engineering*, Vol. BME-17, No. 2, April 1970; "Optical Diffusion in Blood," by Curtis C. Johnson, *IEEE Transactions on Biomedical Engineering*, Vol. BME-17, No. 2, April 1970 and "Optical Scattering in Blood," by Narayanan R. Pisharoty, (Published Doctoral Dissertation), No. 7124861, University Microfilms, Ann Arbor, Mich. (1971).

There has been considerable interest in recent years in the development of an oximeter which is capable of using reflected light to measure blood oxygen saturation. A reflectance oximeter would be especially useful for measuring blood oxygen saturation in portions of the patient's body which are not well suited to transmission measurements. A theoretical discussion of a basis for the design of a reflectance oximeter is contained in "Theory and Development of a Transcutaneous Reflectance Oximeter System for Noninvasive Measurements of Arterial Oxygen Saturation," by Yitzhak Mendelson (Published Doctoral Dissertation), No. 8329355, University Microfilms, Ann Arbor, Mich. (1983). In addition, reflectance oximetry devices and techniques are shown generally in U.S. Pat. Nos. 4,447,150; 4,086,915; and 3,825,342. Recent work by the present inventor and other investigators has shown that it is possible to obtain accurate indications of blood oxygen saturation using reflectance oximetry techniques. One of the difficulties with previous reflectance oximeters, however, is the need to have prior information relating to the oxygen content of the patient's blood in order to construct an oxygen saturation reference curve for that particular patient. Such information is typically obtained by removing and analyzing a sample of the patient's blood or by measuring the patient's oxygen saturation with another monitoring device, such as a transmission oximeter.

SUMMARY OF THE INVENTION

The present invention overcomes the difficulties of the prior art by providing a noninvasive backscatter oximeter which is capable of providing accurate indications of a patient's blood oxygen saturation without the need for obtaining prior information relating to the oxygen content of the patient's blood. The oximeter of the present invention determines the blood oxygen saturation of a patient's blood by a noninvasive optical technique which takes advantage of differences in the absorption spectra of hemoglobin and oxyhemoglobin. In the preferred embodiment, the invention comprises means for illuminating the patient's blood with light at four different wavelengths, means for measuring the intensity of the reflected light at each of the four wavelengths after contact with the blood and means for correlating the intensity of the reflected light with the oxygen saturation of the patient's blood. The invention oximeter is calibrated by pressing an optical sensor firmly against the patient's tissue to remove substantially all of the blood from the tissue. The tissue is then illuminated with the light at four different wavelengths and reflected light signals are detected and processed to obtain information relating to the optical properties of the patient's tissue. The pressure of the sensor against the tissue is then reduced to allow blood to return to the tissue and subsequent measurements of light reflected by the blood are correlated with blood oxygen saturation using mathematical relationships for arterial and venous oxygen saturation.

BRIEF DESCRIPTION OF THE DRAWING

FIG. 1 is a schematic block diagram of a simplified embodiment of the backscatter blood oxygen saturation monitoring system of the present invention.

DETAILED DESCRIPTION OF THE PREFERRED EMBODIMENT

Referring to FIG. 1 the noninvasive monitoring system 10 of the present invention is shown in its preferred embodiment. A monitoring probe 12 is positioned over a portion of the patient's tissue 14 such that light produced by four light emitting diodes (LED) 16, 18, 20 and 22 will be reflected by blood in the tissue and detected by a photodetector 24. Two of the LEDs, e.g. 16 and 18, emit light in the red spectrum and the other two LEDs, e.g. 20 and 22, emit light in the infrared spectrum. In the preferred embodiment, LEDs 16 and 18 emit light at 660 and 680 nm (red), respectively, while LEDs 20 and 22 emit light at 800 and 900 nm (infrared), respectively. However, the invention is not intended to be limited to the specific wavelength of light produced by the above-mentioned LEDs. Proper operation of the invention requires only that two of the light sources have a wavelength for which the absorption coefficients of hemoglobin and oxyhemoglobin are different.

Operation of the LEDs is controlled by a timing control circuit 26 which causes the LEDs to emit an ordered sequence of pulses of light at the above-mentioned wavelengths. These pulses of light are reflected by blood contained in the patient's tissue and are detected by a photodetector 24. The reflected light signals detected by detector 24 are converted to a series of electrical impulses which are demultiplexed by demultiplexer 28 and converted to digital signals by analog-to-digital converter 30. The resulting sequence of digital signals is then fed into a microprocessor 32 and processed in conjunction with mathematical relationships, described in greater detail below, to obtain an indication of the patient's arterial and venous blood oxygen saturations. The resulting values are then displayed on an appropriate output display 34. The functional features of the above-described system can be accomplished through the use of electronic components and techniques which are known in the art.

The techniques used to calculate oxygen saturation in the invention system can be understood from the following discussion of the relationships between the reflected light signals detected by the system. The following equation describes light reflection from a turbid, both absorbing and scattering, medium:

$$R_d = \left[\frac{s + k - \sqrt{k(k+2s)}}{s}\right]\left[\frac{1 - e^{-2d\sqrt{k(k+2s)}}}{1 - Ae^{-2d\sqrt{k(k+2s)}}}\right]$$

$$A = \frac{s + k + \sqrt{k(k+2s)}}{s + k - \sqrt{k(k+2s)}}$$

where:
$R_d$—reflection of light from a medium.
$d$—thickness of the medium.
$s$—scattering coefficient of medium.
$k$—absorption coefficient of medium.

For a backscatter oximeter, the following assumptions can be used to simplify the above equations: (1) tissue thickness can be considered to be very large, and (2) the optical scattering of bloodless tissue is very close to the optical scattering of the perfused tissue at systole and diastole. From the assumption regarding the thickness of the tissue, the following equation can be obtained:

$$R_\infty = \frac{s + k - \sqrt{k(k+2s)}}{s} \text{ at } d = \infty$$

Information regarding the optical properties of the tissue can be obtained if a "bloodless" calibration is performed. This is done by attaching the sensor 12 to the patient and applying sufficient pressure to the sensor to temporarily remove the blood from the tissue.

Applying the above equation to voltages measured for bloodless tissue and for perfused tissue at systole and diastole, the following equations can be formed:

$$V_t = I_0 R_\infty = \frac{I_0[s_t + k_t - \sqrt{k_t(k_t + 2s_t)}]}{s_t} \text{ for bloodless tissue}$$

$$V_d = I_0 R_\infty = \frac{I_0[s_d + k_d - \sqrt{k_d(k_d + 2s_d)}]}{s_d} \text{ for perfused tissue at diastole}$$

$s_d = (1 - \Delta_v) s_t + \Delta_v s_v$
$k_d = (1 - \Delta_v) k_t + \Delta_v k_v$
$k_v = C_{Hb}(Os_v HbO2) + (1 - Os_v) Hb)$ $$V_s = I_0 R_\infty = \frac{I_0[s_s + k_s - \sqrt{k_s(k_s + 2s_s)}]}{s_s} \text{ for perfused tissue at systole}$$

$s_s = (1 - \Delta_a) s_d + \Delta_a s_a$
$k_s = (1 - \Delta_a) k_d + \Delta_a k_a$
$k_a = C_{Hb}(Os_a HbO2) + (1 - Os_v) Hb)$ where:
$s_t$—scattering coefficient of bloodless tissue.
$s_d$—scattering coefficient of perfused tissue at diastole.
$s_s$—scattering coefficient of perfused tissue at systole.
$s_a$—scattering coefficient of arterial blood.
$s_v$—scattering coefficient of venous blood.
$k_t$—absorption coefficient of bloodless tissue.
$k_d$—absorption coefficient of perfused tissue at diastole.
$k_s$—absorption coefficient of perfused tissue at systole.
$k_a$—absorption coefficient of arterial blood.
$k_v$—absorption coefficient of venous blood.
$\Delta_a$—fraction of arterial blood in perfused tissue at systole.
$\Delta_v$—fraction of venous blood in perfused tissue at diastole.
$C_{Hb}$—Concentration of hemoglobin in the blood.
HbO2—Optical absorption coefficient for oxygenated hemoglobin.
Hb—Optical absorption coefficient for reduced hemoglobin.
$OS_a$—Oxygen saturation of arterial blood.
$OS_v$—Oxygen saturation of venous blood.
$I_0$—input intensity of light source.
$V_t$—reflectance voltage signal for bloodless tissue.
$V_d$—reflectance voltage signal for perfused tissue at diastole.
$V_s$—reflectance voltage signal for perfused tissue at systole.

If it is assumed that the scattering coefficient of bloodless tissue, perfused tissue at systole and diastole are approximately the same, the following equations can be formed:

$$V_t = \frac{I_0[s_t + k_t - \sqrt{k_t(k_t + 2s_t)}]}{s_t}$$

$$V_d = \frac{I_0[s_t + k_d - \sqrt{k_d(k_d + 2s_t)}]}{s_t}$$

$$V_s = \frac{I_0[s_t + k_s - \sqrt{k_s(k_s + 2s_t)}]}{s_t}$$

By using four light sources of differing wavelengths, a solution can be obtained for $OS_a$:
let:

$$X_i = V_{ti}V_{di}(V_{si} - I_{0i})^2$$

$$Y_i = V_{ti}V_{si}(V_{di} - I_{0i})^2$$

$$Z_i = V_{si}V_{di}(V_{ti} - I_{0i})^2$$

$$\Delta Hb_i = HbO2i - Hb_i$$

$$A_{jkl} = (Y_j - Z_j)(X_lY_k - X_kY_l)$$

$$B_{jkl} = (X_j - Y_j)(Y_lZ_k - Y_kZ_l)$$

$$D_{mno} = \Delta Hb_m\Delta Hb_oHb_nB_{nom} + \Delta Hb_o\Delta Hb_nHb_mB_{mno} + \Delta Hb_n\Delta Hb_mHb_oB_{omn}$$

$$E_{mno} = \Delta Hb_mHb_nHb_o(A_{mno} + B_{nom} + B_{omn}) + \Delta Hb_nHb_oHb_m(A_{nom} + B_{omn} + B_{mno}) + \Delta Hb_oHb_mHb_n(A_{omn} + B_{mno} + B_{nom})$$

$$F_{mno} = Hb_mHb_nHb_o(A_{mno} + A_{nom} + A_{omn} + B_{nom} + B_{mno} + B_{omn})$$

$$G_{mno} = \Delta Hb_m\Delta H_n \Delta Hb_o(A_{mno} + A_{nom} + A_{omn})$$

$$H_{mno} = \Delta Hb_m\Delta Hb_oHb_n A_{nom} + \Delta Hb_oHb_nA_{mno} + \Delta Hb_n\Delta Hb_mHb_o A_{omn}$$

$$a = (E_{123}G_{134} + D_{123}H_{134} - E_{134}G_{123} - D_{134}H_{123})(D_{124}G_{234} - D_{234}G_{124}) - (E_{124}G_{234} + D_{124}H_{234} - E_{234}G_{124} - D_{234}H_{124})(D_{123}G_{134} - D_{134}G_{123})$$

$$b = (F_{123}G_{134} + E_{123}H_{134} - F_{134}G_{123} - E_{134}H_{123})(D_{124}G_{234} - D_{234}G_{124}) - (F_{124}G_{234} + E_{124}H_{234} - F_{234}G_{124} - E_{234}H_{124})(D_{123}G_{134} - D_{134}G_{123})$$

$$C = (F_{123}H_{134} - F_{134}H_{123})(D_{124}G_{234} - D_{234}G_{124}) - (F_{124}H_{234} - F_{234}H_{134})(D_{123}G_{134} - D_{134}G_{123})$$

where:

i—light source 1, 2, 3, and 4, respectively.

jkl—combination of three light sources 123, 231, 312, 134, 341, 413, 124, 241, 412, 234, 342, and 423, respectively.

mno—combination of three light sources 123, 134, 124, and 234, respectively.

The above relation is a quadratic form of an equation relating the voltages for the bloodless tissue and the perfused tissue at diastole and systole to $OS_a$. The above equation will produce two solutions. One of the solutions will be approximately equal to zero. The other solution will be the correct solution for $OS_a$. Calculation of $OS_a$ using the abovedescribed relation can be easily accomplished using computer programming techniques which are known in the art. An Arterial Blood Oxygen Saturation Correlation Program for calculating $OS_a$ has been shown in FIG. 1 as providing an input to the microprocessor 32.

Once the value of $OS_a$ is obtained as shown above, a solution can be obtained for $O_v$:

let:

$$L_p = OS_a HbO2_p + (1 - OS_a)Hb_p$$

$$M_{qr} = \Delta Hb_r(X_r - Y_r)(Y_q - Z_q)L_q - \Delta Hb_q(X_q - Y_q)(Y_r - Z_r)L_r$$

$$N_{qr} = \Delta Hb_r Y_r(Y_q - Z_q)L_q - \Delta Hb_q Y_q(Y_r - Z_r)L_r$$

$$O_{qr} = Hb_r(X_r - Y_r)(Y_q - Z_q)L_q - Hb_q(X_q - Y_q)(Y_r - Z_r)L_r$$

$$P_{qr} = \Delta Hb_r Y_r(Y_q - Z_q)L_q - \Delta Hb_q Y_q(Y_r - Z_r)L_r + (Z_q(Y_r - Z_r) - Z_r(Y_q - Z_q))L_q L_r$$

$$d = M_{12}N_{13} - M_{13}N_{12}$$

$$e = N_{13}O_{12} + M_{12}P_{13} - N_{12}O_{13} - M_{13}P_{12}$$

$$f = O_{12}P_{13} - O_{13}P_{12}$$

where:

p—light source 1, 2, and 3, respectively.

qr—combination of two light sources 12 and 13, respectively.

$$OS_v = \frac{-e \pm \sqrt{e^2 - 4df}}{2d}$$

The above equation will produce two solutions. One of the solutions will be approximately equal to $OS_a$. The other solution will be the correct solution for $OS_v$. Calculation of $OS_v$ using the above-described relation can be easily accomplished using computer programming techniques which are known in the art. A Venous Blood Oxygen Saturation Correlation Program for calculating $OS_v$ has been shown in FIG. 1 as providing an input to the microprocessor 32.

While the invention method and apparatus for noninvasive monitoring of arterial blood oxygen saturation has been described in connection with the preferred embodiment, it is not intended to be limited to the specific form set forth herein, but on the contrary, it is intended to cover such alternatives, modifications and equivalents as may be reasonably included within the spirit and scope of the invention as defined by the appended claims.

We claim:

1. A blood oxygen saturation monitoring system comprising:
   a source of electromagnetic radiation at first, second, third and fourth wavelengths;
   means for positioning said source of electromagnetic radiation to illuminate a sample of blood;
   sensing means for receiving electromagnetic radiation reflected by said sample of blood and producing an electrical output signal corresponding to the components of the reflected portions of said electromagnetic radiation at said first, second, third, and fourth wavelengths;
   means for calculating a product of said electrical signals, said product being in the form of a quadratic equation relating said reflected portions of said electromagnetic radiation at said first, second, third, and fourth wavelengths to the oxygen saturation in said blood and for correlating said product with the oxygen saturation of said blood.

2. The monitoring system according to claim 1, wherein said first, second, third and fourth sources of electromagnetic radiation comprise first, second, third and fourth light emitting diodes.

3. The monitoring system according to claim 2, wherein said first and second light emitting diodes provide electromagnetic radiation having a wavelength corresponding to red and said third and fourth light emitting diodes provide electromagnetic radiation having a wavelength corresponding to infrared.

4. The monitoring system according to claim 3, wherein said first and second light emitting diodes produce electromagnetic radiation at approximately 660 and 680 nanometers, respectively and said third and fourth light emitting diodes produce electromagnetic radiation at 800 and 900 nanometers, respectively.

5. A method for determining the oxygen saturation of arterial blood, comprising the steps of:

illuminating a sample of said blood with electromagnetic radiation at first, second, third, and fourth wavelengths;

collecting electromagnetic radiation reflected by said sample of blood and producing electrical signals corresponding to the reflected components of said electromagnetic radiation at said first, second, third and fourth wavelengths;

calculating a product of said electrical signals, said product being in the form of a quadratic equation relating said reflected portions of said electromagnetic radiation at said first, second, third, and fourth wavelengths to the oxygen saturation in said blood and correlating said product with the oxygen saturation of said blood.

6. The method accroding to claim 5, wherein said first, second, third and fourth sources of electromagnetic radiation comprise first, second, third and fourth light emitting diodes.

7. The method according to claim 6, wherein said first and second light emitting diodes provide electromagnetic radiation having a wavelength corresponding to red and said third and fourth light emitting diodes provide electromagnetic radiation having a wavelength corresponding to infrared.

8. The method according to claim 7, wherein said first and second light emitting diodes produce electromagnetic radiation at approximately 660 and 680 nanometers, respectively and said third and fourth light emitting diodes produce electromagnetic radiation at 800 and 900 nanometers, respectively.

* * * * *